United States Patent
Minami et al.

(10) Patent No.: US 11,774,346 B2
(45) Date of Patent: Oct. 3, 2023

(54) RECEPTOR RESPONSE MODULATION METHOD, AND MEASURING DEVICE USING RECEPTOR RESPONSE MODULATION

(71) Applicant: NATIONAL INSTITUTE FOR MATERIALS SCIENCE, Ibaraki (JP)

(72) Inventors: Kosuke Minami, Ibaraki (JP); Gaku Imamura, Ibaraki (JP); Kota Shiba, Ibaraki (JP); Genki Yoshikawa, Ibaraki (JP)

(73) Assignee: NATIONAL INSTITUTE FOR MATERIALS SCIENCE, Ibaraki (JP)

( * ) Notice: Subject to any disclaimer, the term of this patent is extended or adjusted under 35 U.S.C. 154(b) by 431 days.

(21) Appl. No.: 17/057,747

(22) PCT Filed: Jun. 4, 2019

(86) PCT No.: PCT/JP2019/022088
§ 371 (c)(1),
(2) Date: Nov. 23, 2020

(87) PCT Pub. No.: WO2019/244613
PCT Pub. Date: Dec. 26, 2019

(65) Prior Publication Data
US 2021/0199563 A1     Jul. 1, 2021

(30) Foreign Application Priority Data
Jun. 19, 2018   (JP) ................................ 2018-115702

(51) Int. Cl.
*G01N 19/00*     (2006.01)
*G01N 5/02*      (2006.01)

(52) U.S. Cl.
CPC ............... *G01N 19/00* (2013.01); *G01N 5/02* (2013.01)

(58) Field of Classification Search
CPC .................................. G01N 19/00; G01N 5/02
See application file for complete search history.

(56) References Cited

U.S. PATENT DOCUMENTS

| | | | | |
|---|---|---|---|---|
| 3,949,599 A * | 4/1976 | Kruishoop | ......... | G01N 33/0026 73/28.01 |
| 5,255,072 A | 10/1993 | Mikasa et al. | | |

(Continued)

FOREIGN PATENT DOCUMENTS

| | | |
|---|---|---|
| WO | 2009/071900 | 6/2009 |
| WO | 2011/148774 | 12/2011 |

OTHER PUBLICATIONS

Extended European Search Report dated Jan. 24, 2022, in corresponding European Patent Application No. 19823067.4.

(Continued)

*Primary Examiner* — Kristina M Deherrera
*Assistant Examiner* — Fatemeh Esfandiari Nia
(74) *Attorney, Agent, or Firm* — Wenderoth, Lind & Ponack, L.L.P.

(57) ABSTRACT

In an analysis of a fluid component using a nanomechanical sensor covered with a receptor, the same receptor is caused to express different response characteristics. In a measuring system of analyzing a response when a sample gas and a purge gas are supplied to a nanomechanical sensor while switching the sample gas and the purge gas, a gas (external gas) different from both gases is mixed into a gas channel and supplied to the sensor for measurement. Since a response characteristic of a receptor is modulated by mixing of the external gas, the object described above is achieved.

11 Claims, 4 Drawing Sheets

(56) References Cited

U.S. PATENT DOCUMENTS

| | | | |
|---|---|---|---|
| 2005/0150280 A1* | 7/2005 | Tang | G01N 33/54346 |
| | | | 73/105 |
| 2013/0133433 A1 | 5/2013 | Yoshikawa et al. | |
| 2019/0041317 A1* | 2/2019 | Hellgren | G01N 33/225 |

OTHER PUBLICATIONS

Communication pursuant to Article 94(3) EPC dated Nov. 2, 2022 in European Patent Application No. 19823067.4.
International Search Report (ISR) dated Sep. 10, 2019 in International (PCT) Application No. PCT/JP2019/022088.
Communication to pursuant to Article 94(3) EPC dated Apr. 11, 2023 in corresponding European Patent Application No. 19823067.4.

* cited by examiner

Broken Line: External Gas Supplied
Solid Line: No External Gas Supplied

Fig. 4

Broken Line: External Gas Supplied
Solid Line: No External Gas Supplied

RECEPTOR RESPONSE MODULATION METHOD, AND MEASURING DEVICE USING RECEPTOR RESPONSE MODULATION

TECHNICAL FIELD

The present invention relates to a method for modulating a response of a receptor that is used for a nanomechanical sensor such as a surface stress sensor and indicates a response such as a change in surface stress by adsorbing a component in a fluid supplied to the nanomechanical sensor. The present invention further relates to a device for performing measurement using such a modulation method.

BACKGROUND ART

Various sensors have been studied in order to detect various components in a gas or a liquid. As one of the sensors, there is a nanomechanical sensor having a receptor that adsorbs a component in a fluid, the nanomechanical sensor detecting changes in various physical parameters caused to the receptor due to adsorption and desorption of such a component. As one of such nanomechanical sensors, a surface stress sensor is known which detects a stress generated in a membrane of the receptor as a change in surface stress by expansion/contraction of the membrane due to adsorption/desorption of various components. As a concrete structure of the surface stress sensor, a cantilever-shaped sensor has been studied so far. However, in recent years, a surface stress sensor called a Membrane-type Surface stress Sensor (MSS) has drawn attention which supports a periphery of a two-dimensionally spread membrane at a plurality of points, concentrates a surface stress applied to a surface of the membrane on the support points, and thereby can measure a surface stress with high sensitivity (Patent Literature 1).

There are a large variety of substances to be detected, which are expected in the nanomechanical sensor typified by the surface stress sensor or the like. Therefore, in order to identify these substances using the nanomechanical sensor, many types of receptors having different response characteristics are required. However, the receptor requires high sensitivity to a substance to be detected, stability after repeated use, durability to a substance contained in a sample fluid or a purging fluid, stability that causes no deterioration or no characteristic change even after repeated use, and the like. Therefore, it is not easy to increase the types of chemical substances or compositions that can be used as the receptor.

SUMMARY OF INVENTION

Technical Problem

An object of the present invention is to modulate various response characteristics of a receptor for a nanomechanical sensor to a sample fluid so as to have a response characteristic different from that of the original receptor.

Solution to Problem

One aspect of the present invention provides a receptor response modulation method including: a step of supplying a fluid to be measured that contains a substance to be measured and may contain a first fluid as an optional component, and a second fluid that does not contain the substance to be measured to a nanomechanical sensor having a receptor on a surface thereof while switching the fluid to be measured and the second fluid; a step of mixing a third fluid different from the first fluid and the second fluid into at least one of the fluid to be measured and the second fluid on a flow channel through which the fluid to be measured and the second fluid are sent to the nanomechanical sensor; and a step of performing measurement of the substance to be measured based on an output signal obtained from the nanomechanical sensor in which a response characteristic of the receptor has been modulated by the mixing of the third fluid.

Here, the concentration of the mixed third fluid in the fluid to be measured may be the same as that in the second fluid.

In addition, the mixing of the third fluid may be selectively performed, and
    the measurement of the substance to be measured may be performed based on both
    a first output signal obtained from the nanomechanical sensor by supplying the fluid to be measured and the second fluid that have been mixed with the third fluid, and
    a second output signal obtained from the nanomechanical sensor by supplying the fluid to be measured and the second fluid that have not been mixed with the third fluid.

In addition, the measurement for obtaining the first output signal and the measurement for obtaining the second output signal may be continuously performed using the same device.

In addition, the measurement for obtaining the first output signal and the measurement for obtaining the second output signal may be performed at different times.

In addition, the fluid to be measured, the first fluid, the second fluid, and the third fluid may be gases.

Alternatively, the fluid to be measured, the first fluid, the second fluid, and the third fluid may be liquids.

In addition, each of the first fluid and the second fluid may be selected from the group consisting of nitrogen, air, and a noble gas.

In addition, the fluid to be measured may further contain the second fluid.

In addition, the nanomechanical sensor may be a surface stress sensor.

In addition, the surface stress sensor may be a membrane-type surface stress sensor.

Another aspect of the present invention provides a measuring device using modulation of a receptor response by a third fluid, the measuring device including: a nanomechanical sensor having a receptor on a surface thereof; a fluid supplying system of supplying a fluid to be measured that contains a substance to be measured and may contain a first fluid as an optional component, and a second fluid that does not contain the substance to be measured to the nanomechanical sensor while switching the fluid to be measured and the second fluid; and a third fluid mixing system of mixing the third fluid different from the first fluid and the second fluid into at least one of the fluid to be measured and the second fluid, in which measurement of the substance to be measured is performed based on an output signal obtained from the nanomechanical sensor in which a response characteristic of the receptor has been modulated by the mixing of the third fluid.

Advantageous Effects of Invention

According to the present invention, since a receptor can function as a receptor having a response characteristic different from the response characteristic of the receptor, the types of receptors that can be selected can be substantially increased. In addition, when the modulation of the response characteristic is an improvement in sensitivity, a specific substance to be measured can be measured with higher sensitivity without development of a novel receptor.

DESCRIPTION OF EMBODIMENTS

According to one aspect of the present invention, when a fluid to be measured (sample fluid) that contains a substance to be measured (sample) and may contain a first fluid as an optional component is supplied to a nanomechanical sensor, and this sample is measured based on a response of the nanomechanical sensor to the fluid to be measured, a third fluid (external fluid) different from the first fluid that may be contained as an optional component in the fluid to be measured is selectively mixed with the fluid to be measured before the fluid to be measured is supplied to the nanomechanical sensor. These fluids may be gases or liquids. However, in order to simplify description, the fluids will be described below mainly as gases. Of course, the description of only gases does not lose generality.

Note that the general expressions of "first fluid (first gas)" and "third fluid (third gas)" have been used above. However, as the "first fluid", an inert fluid is usually used in a sense that the first fluid is not too much strongly bonded to the receptor. When a gas is used as the fluid, a nitrogen gas, air, or a noble gas is often used as the first gas. Such a gas is used as a carrier gas for causing a sample to flow in a measurement system or as a purge gas for washing away the sample adsorbed on the receptor to return the receptor to an initial state (or bring the receptor closer to an initial state). Of course, a gas other than nitrogen, air, and a noble gas can be used as the first gas (first fluid) depending on the properties of a sample to be measured or a receptor.

It should be noted here that a sensor having a receptor on a surface thereof by coating or the like is not used immediately after being stored in a vacuum for a long time. Therefore, before a sample gas is supplied to the sensor, the sensor adsorbs a molecule in a gas existing as an environment of the sensor (referred to as "environmental gas") to reach an equilibrium state. Therefore, when the sample gas is supplied to the sensor, adsorption of a component molecule (sample molecule) in the sample gas does not start from a state where nothing is adsorbed on the receptor, but is performed in a form of gradually replacing an environmental gas molecule already adsorbed. Here, the environmental gas is usually the same as a purge gas.

The measurement using the nanomechanical sensor often uses a measuring method for repeatedly supplying a fluid to be measured (sample gas) and a second fluid (purge gas) not containing a substance to be measured (sample) while alternately switching the fluid to be measured and the second fluid. Use of this measuring method not only makes it easy to determine a baseline of an output signal (hereinafter, referred to as "sensor signal", or further simply referred to as "signal") of the nanomechanical sensor for a sample gas, but also makes it possible to obtain not only a static response characteristic such as a signal at the baseline (stable (saturated) signal obtained by causing a purge gas to flow for a sufficiently long time) or a final signal for the sample gas (stable (saturated) signal obtained by causing a sample gas to flow for a sufficiently long time) but also a dynamic response characteristic such as a signal change due to switching between the sample gas and the purge gas, that is, a signal transient state. Therefore, the amount of information available for measurement of a sample increases. In Example of the present application, the above-described alternate switching between a sample gas and a purge gas was performed, and a signal appearing in response thereto was obtained. In an embodiment as described in Example below, as the "second fluid", like the "first fluid" above, an inert fluid is usually used in a sense that the second fluid is not too much strongly bonded to the receptor. When a gas is used as the fluid, a nitrogen gas, air, or a noble gas can be used as the second gas. It should be noted here that the second fluid is not necessarily required to be inert in all respects, and may be any one that is not significantly harmful to a specific measurement or a member constituting a measurement system thereof. For example, it is often convenient to use air as the first fluid, but oxygen, which is one of main components of the atmosphere, is a chemically active gas. In a case of a liquid, use of water, which is not considered to be inert, as the second fluid is also useful in many respects. As described above, suitability of the second fluid for activity should be determined from a viewpoint of convenience for each individual measurement as a whole. Note that the same applies to the first fluid. In the present embodiment, the "third fluid" is a fluid different from the first fluid and the second fluid, and the third fluid is selectively mixed into at least one of the sample gas and the second fluid on a flow channel on through the sample gas and the second fluid are sent to the nanomechanical sensor, and then is supplied to the nanomechanical sensor.

Note that description will be made to make sure. Depending on a combination of a sample gas, a purge gas, and a receptor, and other measurement conditions, a transient state of a signal due to the above-described switching between the sample gas and purge gas may end in a short time, and a stable state where a signal hardly fluctuates may be maintained until next switching. Alternatively, when the transient state continues for a long time, next switching may occur before the transient state enters the stable state, and a next transient state may thereby start. It should be noted that even when a signal does not have a stable state (sawtoothed signal waveform) like the latter, a sample can be measured without problems based on a dynamic response characteristic appearing there.

In the present invention, in a form in which a gas is used as a fluid, the above-described modulation of a response characteristic of a receptor is performed by mixing a "third fluid (third gas)" with a fluid to be measured (sample gas). However, as the third gas, in principle, any gas that causes such modulation can be used without limitation. Of course, it is preferable to use a combination of a third gas and a receptor, having no adverse effect such as an unstable measurement result due to the mixing or promotion of deterioration of the receptor. The "third gas" is not limited thereto, but in Example described below, ethanol, heptane, and toluene were used, as necessary. Note that the first gas and the second gas used in Example were both nitrogen gases.

The principle of the present invention will be described below.

In the nanomechanical sensor, a sensor signal is considered to be generated at least through the following processes, although there are still unclear parts about an operating principle thereof:

I: Adsorption of a sample gas molecule on a surface of a sensitive membrane and diffusion of the sample gas molecule into the sensitive membrane II: Continuous dynamic equilibrium change between the sensitive membrane and a sensor element and dissipation of a viscoelastic effect III: Diffusion of the sample gas molecule from the inside of the sensitive membrane to a surface of the sensitive membrane and desorption of the sample gas molecule from the surface of the sensitive membrane By repeating these processes I to III, a series of sensor signal waveforms can be obtained.

In the processes of I and III above, a sample gas molecule is not adsorbed on/diffused to a place where there is nothing, but is continuously replaced with an "environmental gas molecule" that has reached an equilibrium state through adsorption on/internal diffusion to a sensitive membrane in advance. This environmental gas is also called "purge gas". In general, nitrogen, air, a noble gas, or the like is often used as the environmental gas. It is not usually attempted to modulate a sensor signal by changing the environmental gas.

Therefore, in the present invention, by positively changing the environmental gas, behavior of a sample gas molecule on a surface of a sensitive membrane or in the inside of the sensitive membrane is changed to obtain different sensor signals. As a result, even when the same sensitive membrane type is used, the same sensitive membrane type can be used as if the same sensitive membrane type is another sensitive membrane type by changing the environmental gas.

From another viewpoint, a signal obtained through the above processes I to III can be considered to be a "difference" between a state where a sample gas is adsorbed and a state where an environmental gas is adsorbed, and "dynamic transition" between these two states. In this case, even if a combination of a sample gas and a sensitive membrane type is not changed, a relative relationship between the two states is changed by changing the environmental gas. Therefore, more diverse signals can be obtained.

Figure 1:
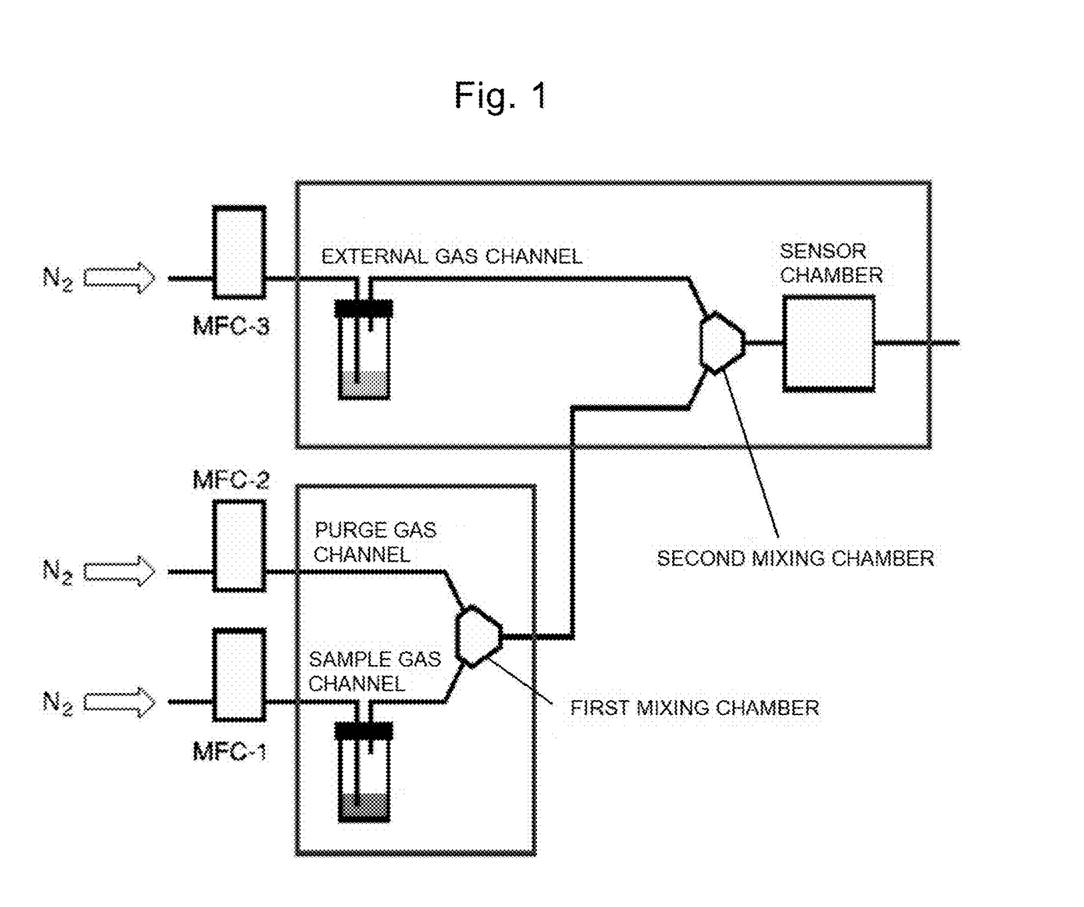
FIG. 1 is a conceptual configuration diagram of a measuring device used in Example.

Next, a measuring device that can be used for performing the measuring method of the present invention will be described. FIG. 1 illustrates a conceptual configuration of an example of such a device. From the left end to the front of a sensor chamber located on the upper right in FIG. 1, an example of a structure of a gas supply system for mixing three types of gases used for measurement and supplying the mixed gases to the sensor chamber is illustrated. A lower part of the structure is a sample gas channel for supplying a sample gas, a middle part of the structure is a purge gas channel for supplying a second fluid (purge gas (here, a nitrogen gas is used as an example)), and an upper part of the structure is an external gas channel for supplying a third fluid (external gas).

Here, since various types of samples are conceivable, it is necessary to prepare the sample gas channel according to the characteristic of each sample. When the sample is a liquid at room temperature, although it depends on a vapor pressure or the like of a liquid that is a source of a sample gas (sample gas source) at a temperature of a test environment, there are configurations such as: a configuration in which a first fluid (first gas; carrier gas) that does not adversely affect measurement as an optional component is provided to a container containing the sample liquid to send out vapor contained in an upper space (head space) of the container, or the carrier gas is blown into the liquid in the container (bubbling) or the liquid is sprayed in the carrier gas to vaporize the liquid to take out a mixed gas containing vapor of the liquid; a configuration in which by heating the liquid in the container, dropping the liquid onto a heated member, or the like, the liquid is heated to take out vapor generated from the liquid as a sample gas; and a configuration in which heating is performed simultaneously in the above configuration using the carrier gas. When the sample is a gas at room temperature, such a gas can be supplied to the sample gas channel as it is or after being mixed with a carrier gas. Alternatively, even if the sample itself is a gas, for example, when it is easier to handle the sample by providing the sample in a state of being dissolved in some liquid, or by dissolving the sample gas once in a liquid, a sample gas channel configuration similar to that of the liquid sample described above can be adopted. When the sample is a solid at room temperature, or when the sample is supplied as a solid containing a component to be measured by adsorption or the like, a sample gas channel configuration to generate a gas from such a solid sample by an appropriate method can be adopted. For example, when a sample gas is volatilized vigorously from such a solid as it is or by heating the solid, the sample gas may be taken out from a head space in a container containing the solid, or a carrier gas may be introduced from the outside into the head space of the container to positively discharge the sample gas in the head space to the outside. When the solid of the sample is liquefied by heating, the sample gas can be taken out with the same configuration as that described for the case where the sample source is a liquid. As described above, the sample gas channel has various forms depending on a sample. However, this fact itself is not related to the characteristics of the present invention, and therefore further description will be omitted below.

In the sample gas channel illustrated in the lower part of FIG. 1, a liquid sample having relatively low volatility is taken as an example. By introducing a nitrogen gas from a nitrogen gas source (not illustrated) such as a gas cylinder while the flow rate of the nitrogen gas is controlled with a mass flow controller MFC-1, and blowing the nitrogen gas as a carrier gas (first fluid) into the liquid sample in a sample container, the nitrogen gas containing sample vapor (sample gas) is supplied to one input of a first mixing chamber.

In the purge gas channel illustrated in the middle part of FIG. 1, similarly to the sample gas channel, a nitrogen gas is introduced from a nitrogen gas source (not illustrated) such as a gas cylinder while the flow rate of the nitrogen gas is controlled with a mass flow controller MFC-2. The nitrogen gas is supplied as a purge gas (second fluid) to the other input of the first mixing chamber. The gas obtained by uniformly mixing the sample gas channel output and the purge gas output, which is an output of the first mixing chamber, is supplied to one input of a second mixing chamber arranged immediately before (on the upstream side of) a sensor chamber. Here, as can be seen from measurement in Example, MFC-1 and MFC-2 are turned on/off in opposite phases with each other at a predetermined cycle, and the output of the purge gas channel and the output of the sample gas channel are alternately switched and supplied to the first mixing chamber.

The external gas channel at an upper part of FIG. 1 supplies an external gas to the other input of the second mixing chamber. Here, as a form of the external gas to be supplied, the external gas may be supplied as a gas, or may be supplied as a liquid or a solid for generating the external gas. However, such a form of a source of the external gas (external gas source) and a difference in the configuration of the external gas channel due to such a form are the same as those described for the sample gas channel, and therefore duplicate description will be omitted. In the configuration example illustrated in FIG. 1, a liquid external gas source having relatively low volatility is taken as an example. That is, here, like the sample gas channel in the lower part, by introducing a nitrogen gas from a nitrogen gas source (not illustrated) such as a gas cylinder while the flow rate of the nitrogen gas is controlled with a mass flow controller MFC-3, and blowing the nitrogen gas into a liquid in a container for generating the external gas, the nitrogen gas containing an external gas (third fluid) that is vapor of the liquid is supplied to the other input of the second mixing chamber. Note that as the external gas, various substances can be used as necessary. For example, ethanol, heptane, and toluene were used as the external gas in Example described below although it is not intended to be limit the external gas thereto.

The three types of gases introduced in this way (sample gas, purge gas, and external gas) are mixed on a downstream side as FIG. 1 illustrates that these channels are joined together, and then supplied to a sensor chamber containing a nanomechanical sensor having a desired receptor layer. In the above mixing, the individual gases to be mixed are desirably supplied to the sensor chamber while being mixed uniformly. Therefore, as the actual structure of the site where this mixing is performed, not only the three channels are simply joined together here, but some means for promoting the mixing of these gases with each other may be installed. In FIG. 1, the mixing chamber is used as an example of such a means.

In this way, a mixed gas including two types of gases, that is, sample gas+external gas (or sample gas+external gas+carrier gas (a purge gas may be used as a carrier gas)) (hereinafter referred to as sample phase mixed gas) and purge gas+external gas (referred to as purge phase mixed gas) are alternately switched and supplied to the sensor chamber. Note that such a configuration for supplying a gas is not limited to that illustrated in FIG. 1, and various modifications can be considered. For example, a valve or the like for closing or switching a flow channel may be arranged in the flow channel although not being clearly illustrated in FIG. 1. In addition, in FIG. 1, a driving force for sending a gas to the sensor chamber is a pressure of the purge gas or the carrier gas (a nitrogen gas is used for each of the purge gas and the carrier gas in the example illustrated in FIG. 1) sent from the left side of the figure, but a pump or the like for pushing out a gas to a downstream side and/or sucking a gas from the downstream side may be installed in the channel.

The amount of the external gas in each of the two types of gases, the sample phase mixed gas and the purge phase mixed gas, which are alternately switched and supplied to the sensor chamber, can be freely set according to various requirements, for example, such that an effect of mixing the external gas is sufficiently exhibited. For example, the concentrations of the external gas in the gases of both phases may be the same as each other although not being limited thereto. When the carrier gas (which may be a purge gas) is mixed into the sample phase mixed gas, the concentration of the external gas only to the carrier gas+external gas components in the sample phase mixed gas may be the same as the concentration of the external gas in the purge phase mixed gas. Of course, the concentrations of the external gas do not have to be the same in either of the above two cases. In an extreme case, the external gas does not have to be mixed into either of the gasses of both phases.

Note that there is one point to be noted here regarding switching between the sample phase mixed gas and the purge phase mixed gas. From the above description, it may be understood that switching between both gases is performed immediately at the time of switching, but this is just description about control of operation of a means for performing switching, such as a mass flow controller or a valve. It should be noted that the description does not mention that the actual gas in such a controlled switching means and on a downstream side thereof switches instantaneously from one to the other. In other words, the mechanism in the switching means is designed/manufactured to operate at a speed as high as possible. However, actually, due to members of the mechanism, inertia of gases to be switched, and the like, switching occurs to a state of only one gas via a transient state, that is, via a state where both gases are mixed. In addition, since the switching means, a flow channel system on a downstream side thereof, and the internal volume of the sensor chamber cannot be set to zero, even if the switching means performs ideal switching, a gas after switching flows downstream while pushing a gas before switching on the downstream of the switching means. As a result, both gases are mixed at a boundary between both gases due to diffusion of the gases, a vortex generated by flowing of the gases, and the like. As a result, from a viewpoint of the nanomechanical sensor in the sensor chamber, it should be noted that in either of the sample phase and the purge phase, the sensor is not exposed only to a gas of each phase within the entire time period from start to end of the phase, but switching is performed from one gas to the other gas via a transient state where both the sample phase mixed gas and the purge phase mixed gas are mixed with each other. Of course, such a transient state desirably ends in a short time.

The nanomechanical sensor in the sensor chamber generates a sensor signal in response to the gas thus supplied. This sensor signal is sent to a control computer (not illustrated) via an interface. The sensor signal is recorded in the computer, and is variously analyzed, for example. The computer performs output, for example, displays a sensor signal itself and an analysis result thereof, and can provide the output to another device such as a server via a network or the like, as necessary.

In addition to this, the computer can perform various control operations other than acquisition, analysis, and the like of the sensor signal. Of course, a plurality of computers can share roles, but it should be understood that the computer also refers to a group of such computers also in such a case. Examples of control operation other than such acquisition/analysis include control of a measurement sequence. As described above, in actual measurement, it is useful to repeat switching between the sample phase mixed gas and the purge phase mixed gas a plurality of times and to analyze a sensor signal in response to such periodic gas supply. Also, in Example described below, a gas supply sequence of 20 seconds per cycle was repeated, in which the purge phase mixed gas was supplied for 10 seconds and then the sample phase mixed gas was supplied for 10 seconds. At this time, it is necessary to appropriately control valves and pumps (mass flow controllers MFC-1 to MFC-3 in FIG. 1) in the channels for supplying three types of gases.

For example, usually, it is necessary to control valves and pumps such that the flow rate of a gas supplied to the sensor chamber does not change even if the above switching is performed. In addition, as a matter of course, it is necessary to precisely control the compositions of the sample phase mixed gas and the purge phase mixed gas supplied to the sensor chamber. In addition, a series of measurements in which conditions are variously changed (for example, measurements in which the concentration of a sample is changed stepwise) are often performed, but in this case, it is necessary to continue the measurements while sequentially changing the above composition and others. In addition, when a measuring method is adopted in which the concentration of the external gas in a gas supplied to the sensor chamber is maintained at a constant concentration, for example, even if the above switching is performed, this ratio is also maintained by appropriate control of valves and pumps (not shown) in the gas supplying channel by a computer (not shown).

EXAMPLE

Hereinafter, the present invention will be described in more detail with reference to Example. Needless to say, it should be noted that Example described here is merely for helping understanding of the present invention, and the technical scope of the present invention is defined only by the claims.

Measurement was performed for various combinations of an external gas and a sample gas using the measuring device whose conceptual configuration has been described above with reference to FIG. 1. Specific measurement is as follows.

Measurement 1: Four types of gases, water (water vapor), chloroform, acetone, and ethanol were used as sample gases, and measurements were performed for both a case where ethanol was supplied as an external gas and a case where no external gas was supplied.

Measurement 2: Four types of gases, water (water vapor), ethanol, ethyl acetate, and toluene were used as sample gases, and measurements were performed for both a case where heptane was supplied as an external gas and a case where no external gas was supplied.

Measurement 3: Four types of gases, ethanol, ethyl acetate, methylcyclohexane, and propionic acid were used as sample gases, and measurements were performed for both a case where toluene was supplied as an external gas and a case where no external gas was supplied.

Note that conditions common to these measurements were as follows.

Switching of gas: A cycle was repeated in which a sample phase gas (or a sample phase mixed gas) was supplied for 10 seconds (sample supply section), and then a purge phase gas (or a purge phase mixed gas) was supplied for 10 seconds (purge section). The concentration of a sample in a gas supplied to the sensor chamber in the sample supply section was 5%.

Flow rate of gas: Control was performed such that a constant flow rate of 100 sccm was constantly maintained in both the sample supply section and the purge section.

Mixing of external gas: Both a measurement in a case where no external gas was mixed and a measurement in a case where the external gas was mixed were performed. In the measurement in a case where the external gas was mixed, the concentration of the external gas in a gas supplied to the sensor chamber was 40% in both the sample supply section and the purge section. More specifically, external gas amount/total gas amount×100=external gas amount/(purge gas amount+external gas amount)×100=external gas amount/(carrier gas amount+sample gas amount+external gas amount)×100=40%. Therefore, the concentration of the external gas in the purge phase gas (purge section) is the same as that in the sample phase gas (sample supply section).

Temperature of gas: The temperature of a gas supplied to the sensor chamber was maintained at 25° C.

Nanomechanical sensor used: A sensor in which a polymer such as polyvinylpyrrolidone or polyacrylic acid had been applied as a receptor to an MSS designed by the inventor of the present application was used.

Figure 2:
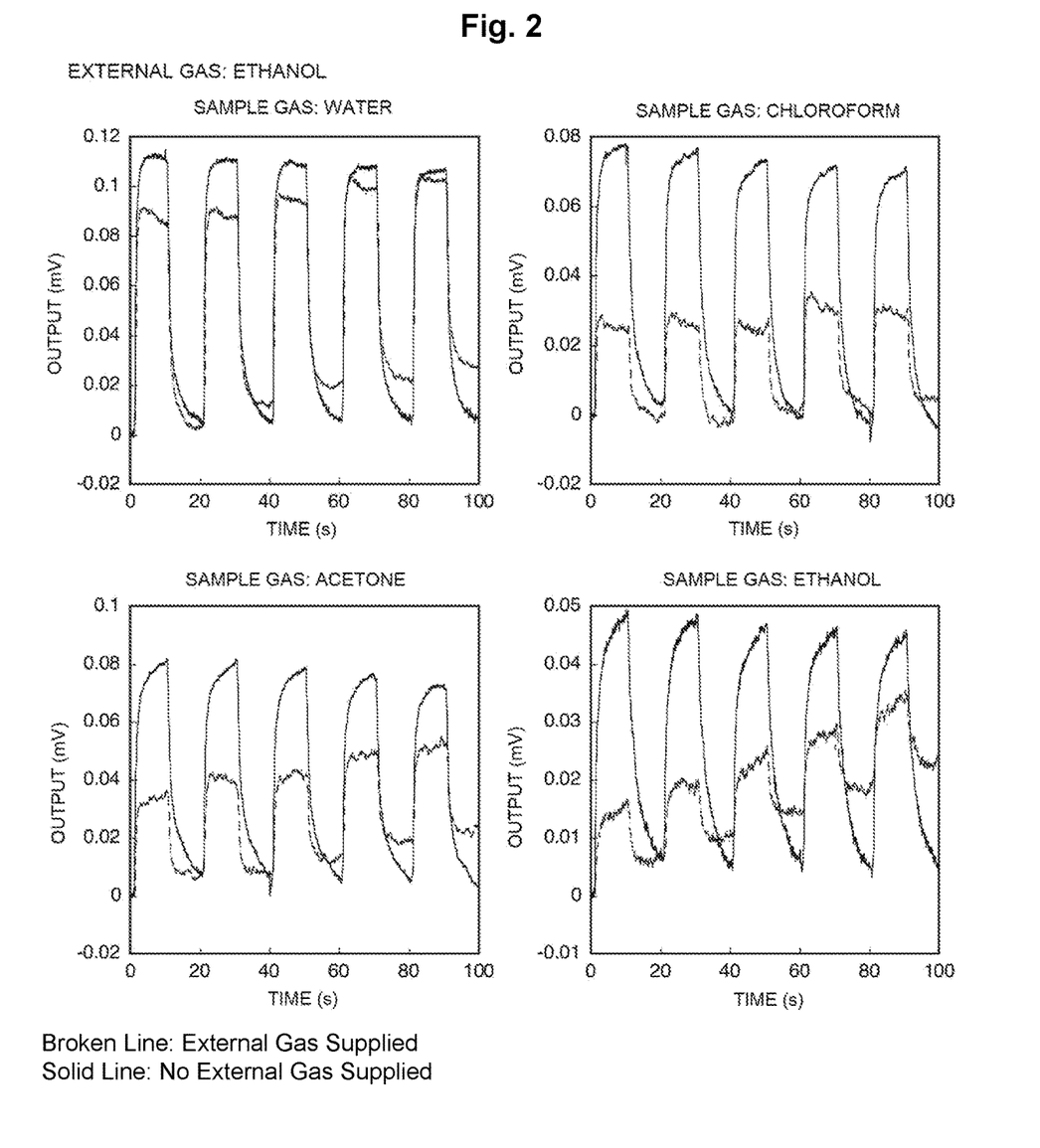
FIG. 2 illustrates graphs of measurement results when ethanol is used as an external gas, and water, chloroform, acetone, and ethanol are used as sample gases.
Figure 3:
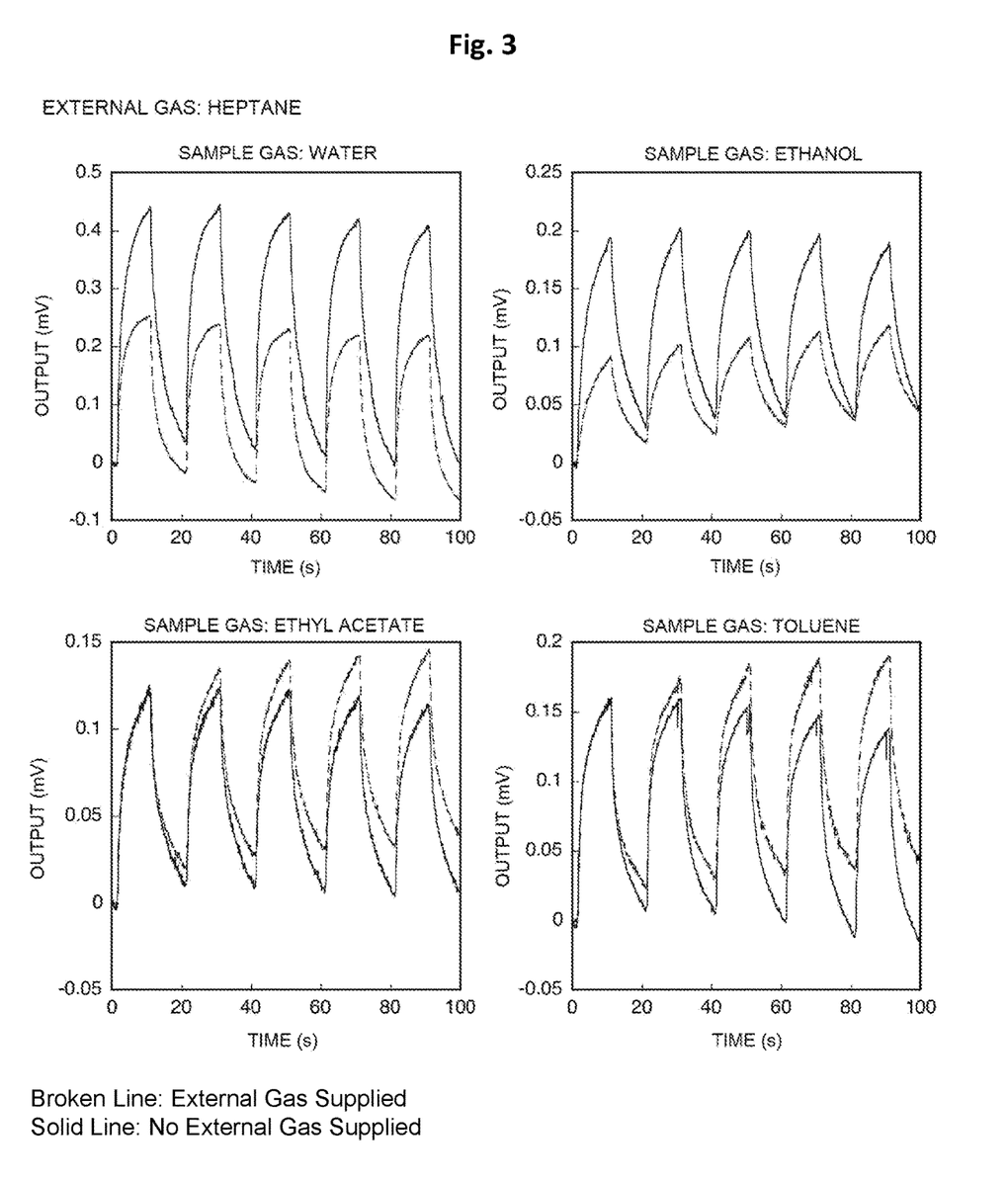
FIG. 3 illustrates graphs of measurement results when heptane is used as an external gas, and water, ethanol, ethyl acetate, and toluene are used as sample gases.
Figure 4:
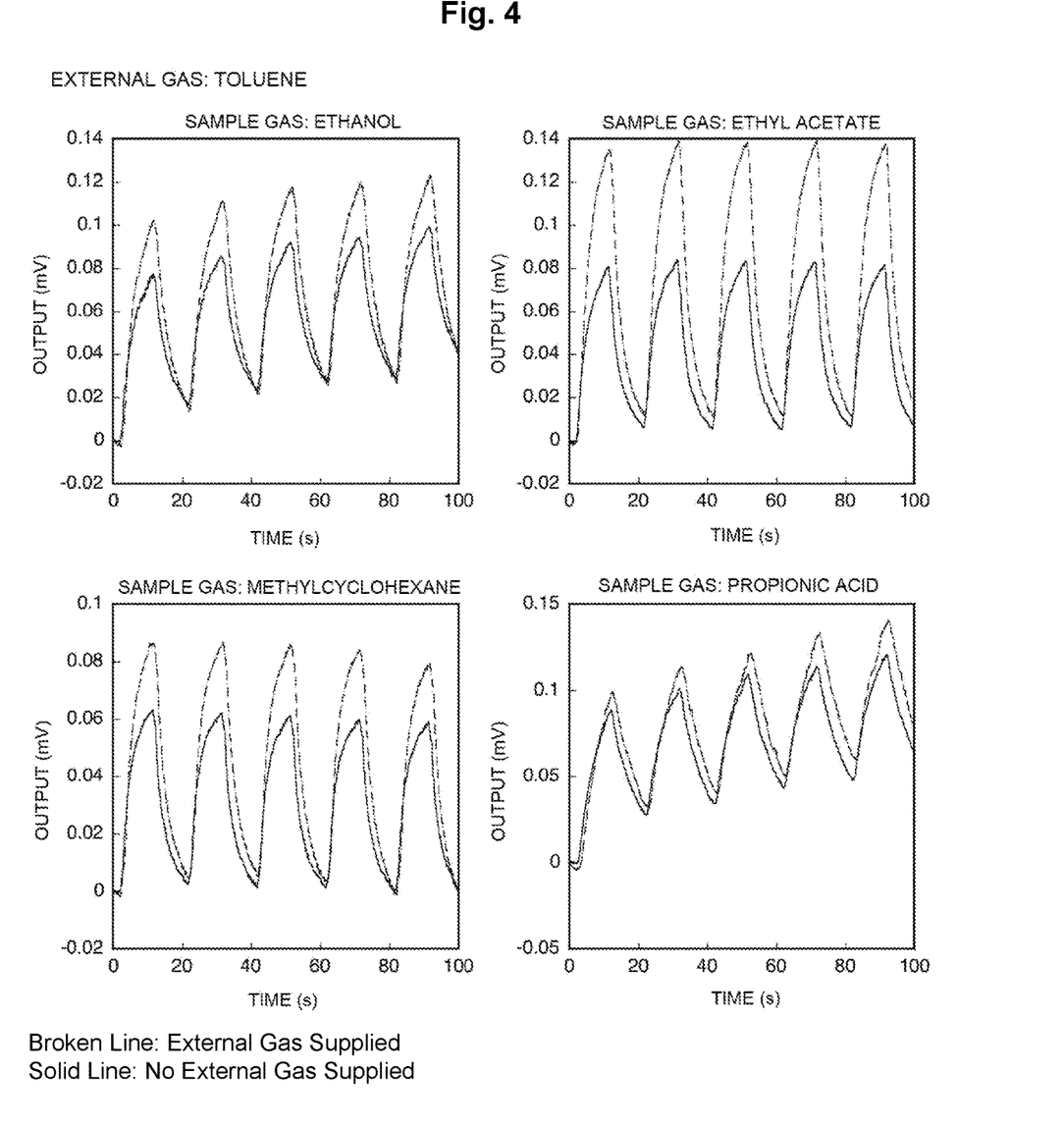
FIG. 4 illustrates graphs of measurement results when toluene is used as an external gas, and ethanol, ethyl acetate, methylcyclohexane, and propionic acid are used as sample gases.

FIGS. 2 to 4 illustrate time-dependent changes of sensor signals in measurements 1 to 3, respectively. Note that in these figures, a broken line represents a sensor signal in a case where the external gas was supplied, and a solid line represents a sensor signal in a case where no external gas was supplied.

As can be seen from these figures, even if the same external gas is supplied, a sensor signal may be large (that is, sensitivity may be high) for a certain sample gas, but a sensor signal may be small for another sample gas. For example, as illustrated in FIG. 3, the sensitivity is high in the combination of heptane as an external gas and ethyl acetate or toluene as a sample gas, but on the other hand the sensitivity is low in the combination of heptane as an external gas and water vapor or ethanol as a sample gas. Thus, it is suggested that an influence of the external gas largely changes depending on a combination of the external gas and the sample gas.

In addition, not only such a static characteristic of response of the receptor to the sample gas (the amplitude of a waveform illustrated in the graph) changes but also a dynamic characteristic of the receptor to the external gas, represented by the waveform in the graphs of FIGS. 2 to 4, changes variously depending on the combination of the external gas and the sample gas. For example, as illustrated in FIG. 2, a case where ethanol is used as the external gas and ethanol and chloroform are used as the sample gas will be described as an example. Here, when ethanol, which is used as the external gas, was supplied as the sample gas, as can be seen from a comparison in FIG. 2 between the waveform in a case where the external gas was supplied and the waveform in a case where no external gas was supplied, both waveforms indicate a similar tendency in having a shape that a sensor signal increased to some extent, and then increased while an increase rate was slightly reduced. However, when the sample gas was changed to chloroform, an effect of supplying the external gas was different. That is, although the external gas was ethanol, which is the same as the above, in a case where the external gas was supplied, a value of the sensor signal increased, approached saturation, and then tended to decrease slightly. Meanwhile, in a case where no external gas was supplied, the increase rate was considerably small even after a value of the sensor signal approached the saturation state, but the increase tendency continued.

INDUSTRIAL APPLICABILITY

As described above, a response characteristic of the receptor to each sample gas variously changes depending on whether or not the external gas is supplied and which external gas is supplied. This corresponds to use/non-use of the external gas, and a change of the type of the external gas equivalently corresponds to changing the used receptor to another one. In addition, for example, in the receptor used in Example, the sensitivity to ethyl acetate becomes about twice by supplying toluene as the external gas as illustrated in FIG. 4. Therefore, an effect of improving the sensitivity to a specific sample can also be obtained by using the external gas. Furthermore, in this case, since the sensitivity to propionic acid hardly changes with the same combination of the receptor and the external gas, use of the external gas may improve selectivity between the samples. Therefore, by further using the external gas for a conventional measurement in the nanomechanical sensor, a wider variety of measurements are possible. Furthermore, even if it is difficult to identify a sample by an ordinary measurement using only the sample gas and the purge gas, by performing both such an ordinary measurement and the measurement of the present invention using an appropriate external gas and combining results thereof, identification may be easy. As a result, it is expected that the present invention will be industrially utilized to a large extent.

CITATION LIST

Patent Literature

Patent Literature 1: WO 2011/148774 A

The invention claimed is:

1. A receptor response modulation method comprising:
a step of supplying a fluid to be measured that contains a substance to be measured and an optional first fluid, and a second fluid that does not contain the substance to be measured to a nanomechanical sensor having a receptor on a surface thereof while switching the fluid to be measured and the second fluid,
a step of mixing a third fluid different from the optional first fluid and the second fluid into each of the fluid to be measured and the second fluid on a flow channel through which the fluid to be measured and the second fluid are sent to the nanomechanical sensor, wherein a concentration of the mixed third fluid in the fluid to be measured is the same as that in the second fluid, and
a step of performing measurement of the substance to be measured based on an output signal obtained from the nanomechanical sensor in which a response characteristic of the receptor has been modulated by the mixing of the third fluid.

2. The receptor response modulation method according to claim 1, wherein
the measurement of the substance to be measured is performed based on both;
a first output signal obtained from the nanomechanical sensor by supplying the fluid to be measured and the second fluid that have been mixed with the third fluid, and
a second output signal obtained from the nanomechanical sensor by supplying the fluid to be measured and the second fluid that have not been mixed with the third fluid.

3. The receptor response modulation method according to claim 2, wherein the measurement for obtaining the first output signal and the measurement for obtaining the second output signal are performed using a same device.

4. The receptor response modulation method according to claim 2, wherein the measurement for obtaining the first output signal and the measurement for obtaining the second output signal are performed at different times.

5. The receptor response modulation method according to claim 1, wherein the fluid to be measured, the optional first fluid, the second fluid, and the third fluid are gases.

6. The receptor response modulation method according to claim 1, wherein the fluid to be measured, the optional first fluid, the second fluid, and the third fluid are liquids.

7. The receptor response modulation method according to claim 1, wherein the fluid to be measured further contains the second fluid.

8. The receptor response modulation method according to claim 1, wherein the nanomechanical sensor is a surface stress sensor.

9. The receptor response modulation method according to claim 5, wherein each of the optional first fluid and the second fluid is selected from the group consisting of nitrogen, air, and a noble gas.

10. The receptor response modulation method according to claim 8, wherein the surface stress sensor is a membrane-type surface stress sensor.

11. A measuring device using modulation of a receptor response by a third fluid, the measuring device comprising:
a nanomechanical sensor having a receptor on a surface thereof,
a fluid supplying system of supplying a fluid to be measured that contains a substance to be measured and an optional first fluid, and a second fluid that does not contain the substance to be measured to the nanomechanical sensor while switching the fluid to be measured and the second fluid, and
a third fluid mixing system of mixing the third fluid different from the optional first fluid and the second fluid into each of the fluid to be measured and the second fluid, wherein
the measuring device is configured to control a concentration of the mixed third fluid in the fluid to be measured and a concentration of the mixed third fluid in the second fluid to be the same as each other, and
measurement of the substance to be measured is performed based on an output signal obtained from the nanomechanical sensor in which a response characteristic of the receptor has been modulated by the mixing of the third fluid.

* * * * *